(12) United States Patent
Solem

(10) Patent No.: US 6,210,430 B1
(45) Date of Patent: Apr. 3, 2001

(54) BY-PASS GRAFT

(76) Inventor: Jan Otto Solem, Nordmannavägen 20, 237 31, Bjärred (SE)

( * ) Notice: Subject to any disclaimer, the term of this patent is extended or adjusted under 35 U.S.C. 154(b) by 0 days.

(21) Appl. No.: 09/192,895

(22) Filed: Nov. 17, 1998

Related U.S. Application Data

(63) Continuation of application No. PCT/SE97/00804, filed on May 16, 1997.

(30) Foreign Application Priority Data

May 17, 1996 (SE) .................................. 9601884

(51) Int. Cl.$^7$ ....................................... A61F 2/06
(52) U.S. Cl. ............................................ 623/1.11
(58) Field of Search .................... 606/151, 152, 606/153, 191–192, 193, 194, 195, 196, 197, 198; 623/1.1, 1.11, 1.12, 1.16, 1.35, 23.64, 23.65, 23.66, 23.7

(56) References Cited

U.S. PATENT DOCUMENTS

| | | | |
|---|---|---|---|
| 5,304,220 | * | 4/1994 | Maginot ........................... 623/1 |
| 5,443,497 | * | 8/1995 | Venbrux ........................... 623/1 |
| 5,456,712 | * | 10/1995 | Maginot ........................... 623/1 |
| 5,571,167 | * | 11/1996 | Maginot ........................... 623/1 |
| 5,643,340 | * | 7/1997 | Nunokawa ....................... 606/153 |
| 5,755,778 | * | 5/1998 | Kleshinski ....................... 606/153 |
| 5,893,886 | * | 4/1999 | Zegdi et al. ..................... 606/153 |
| 5,925,254 | * | 7/1999 | Taylor et al. .................... 606/153 |
| 6,068,654 | * | 5/2000 | Berg et al. ....................... 606/153 |

FOREIGN PATENT DOCUMENTS

8806865 * 9/1988 (WO) ................................. 623/1

* cited by examiner

Primary Examiner—David J. Isabella
(74) Attorney, Agent, or Firm—Browdy and Neimark

(57) ABSTRACT

A branching device for a blood vessel has a sleeve (10), which is radially extensible and has an opening (12) in its circumferential surface, and a collar (11) consisting of a fluid-tight material and fixed to the sleeve before the branching device is used. The collar has on the one hand a shoulder portion (13), which extends at least around the opening in the circumferential surface of the sleeve, and, on the other hand, a neck portion (14) integral with the shoulder portion and projecting radially from the opening in the circumferential surface of the sleeve.

17 Claims, 3 Drawing Sheets

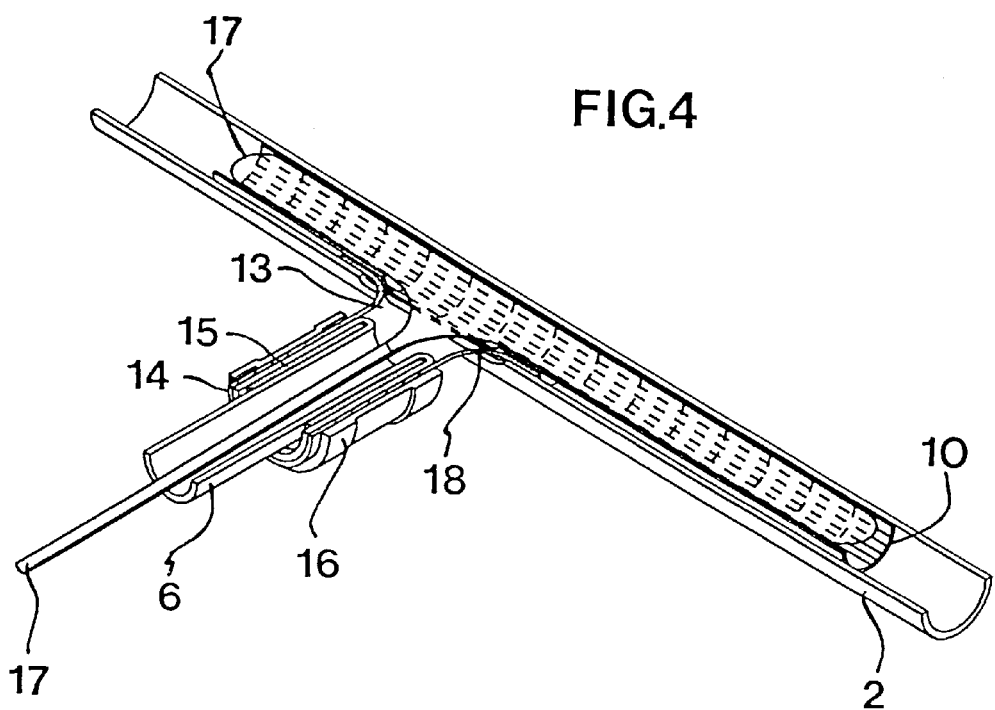
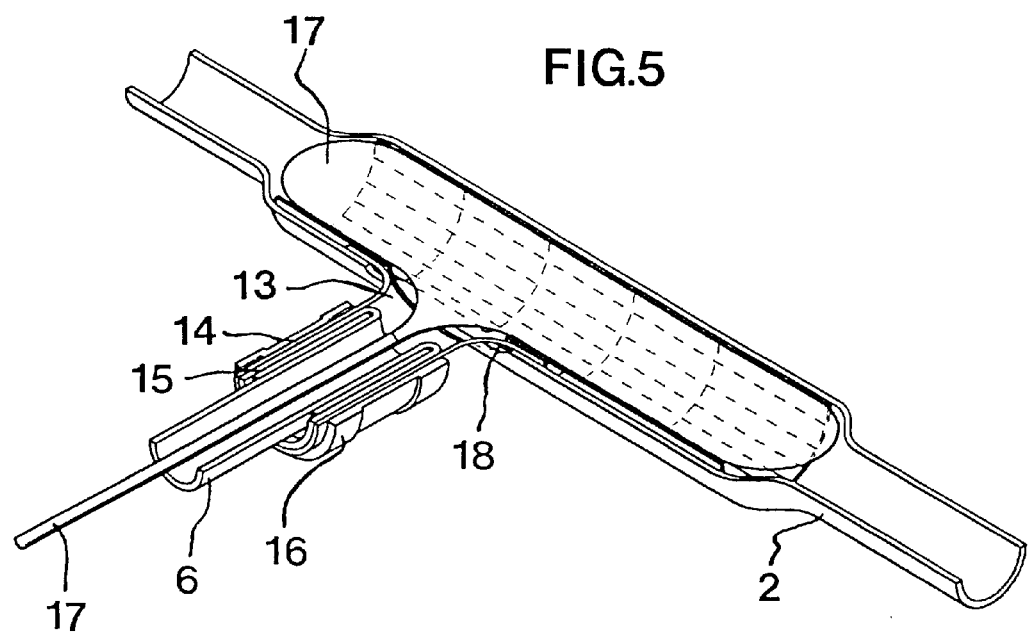

BY-PASS GRAFT

This application is a continuation of copending parent application Ser. No. PCT/SE97/00804, filed May 16, 1997.

FIELD OF INVENTION

The present invention relates generally to the field of vascular surgery and, more specifically, to a branching device for blood vessels, especially for bypass operations on the coronary vessels.

BACKGROUND

An increased flow resistance in the various coronary vessels can jeopardise the oxygen supply to the cardiac muscle. In some cases an expansion of vascular stenosis is possible. If the flow of blood in a vessel is completely or practically completely blocked, the only thing to be done is to bypass the blocked portion to prevent an irreparable injury from arising. Such a bypass operation is usually effected by connecting a new vessel after the blocked point and connecting it to another blood vessel, for instance the aorta, which may give a sufficient flow of blood to the blood vessel after the blocked point.

In practice, such a bypass operation requires the use of a heart-lung machine, i.e. that the heart be temporarily stopped since the bypass operation when connecting, for instance, the two vessels involved requires the heart to be immovable. In consequence of the connecting technique employed and the use of the heart-lung machine, the operation will be relatively time-consuming and not completely without risk.

When larger vessels are involved, it is known from e.g. U.S. Pat. No. 5,456,712 to provide a branch by blocking the vessel by means of balloons on each side of the intended branch point, whereupon an incision is made in the blocked portion of the blood vessel. Then an expanded end of a vascular prosthesis is inserted through the incision and a stent is inserted through the one blocking balloon to a position inside the incision, where finally the stent is expanded by means of a further balloon positioned inside the stent. For completely safe fixing of the expanded end to the area around the incision in the vessel, some sort of suture is used, primarily for connecting the expanded end of the vascular prosthesis with the blood vessel around the incision therein.

The prior-art technique implies that a blocking can be made on each side of the intended branch point, and that the stent can be inserted via the diseased vessel involved and through one of the blocking balloons. In practice, also a fixing of the expanded end of the vascular prosthesis relative to the vessel involved by means of some sort of suture is required.

The technique according to U.S. Pat. No. 5,456,712 is thus not suited for use in thin vessels, such as the coronary vessels, or in other positions where the described blocking by means of a balloon from the inside of the vessel is not possible.

SUMMARY OF INVENTION

The object of the present invention is to provide a simple and reliable bypass of the coronary vessels without necessitating temporary internal blockings, preferably in a manner which can make it possible that the heart-lung machine need not be used, i.e. it should be possible to perform the bypass operation with the heart beating. Most preferably, it should be possible to carry out the operation by applying endoscopy.

According to the invention, this object is achieved by a branching device having a sleeve, which is radially extensible and has an opening in its circumferential surface, and a collar which consists of a fluid-tight material and is fixed to the sleeve before the branching device is used and which has on the one hand a shoulder portion extending at least around the opening in the circumferential surface of the sleeve and, on the other hand, a neck portion integral with the shoulder portion and projecting radially from the opening in the circumferential surface of the sleeve.

The opening in the circumferential surface of the sleeve is preferably arranged unsymmetrically relative to the ends of the sleeve. This confers an advantage since the necessary longitudinal incision in the blocked vessel need not be made longer than the distance from the neck portion to the nearest end of the sleeve, while the sleeve of the branching device can be retained safely in the vessel thanks to the sleeve obtaining a long part (seen from the neck portion), which must thus first be inserted into the opening in the vessel.

After the insertion of the sleeve into the vessel in a reciprocating movement, the short part of the sleeve is positioned completely beyond the opening in the vessel, while the long part of the sleeve covers the main part of the opening in the vessel and besides can extend beyond this a distance of essentially the same length as the short part of the sleeve. Once the sleeve is correctly positioned in the vessel, its position is to be fixed. This is possible according to the invention thanks to the sleeve being radially extensible and retaining its extended shape, i.e. the shape of the sleeve is permanently deformable. This results in an expansion of the vessel, which then clamps the sleeve in place and also clamps the shoulder portion of the collar against the sleeve.

BRIEF DESCRIPTION OF DRAWINGS

The invention will now be described in more detail with reference to the accompanying drawings, in which FIG. 4 shows the device after insertion into the blocked vessel, and FIG. 5 shows the device after fixing in the blocked vessel.

DETAILED DESCRIPTION OF EMBODIMENTS

Figure 1:
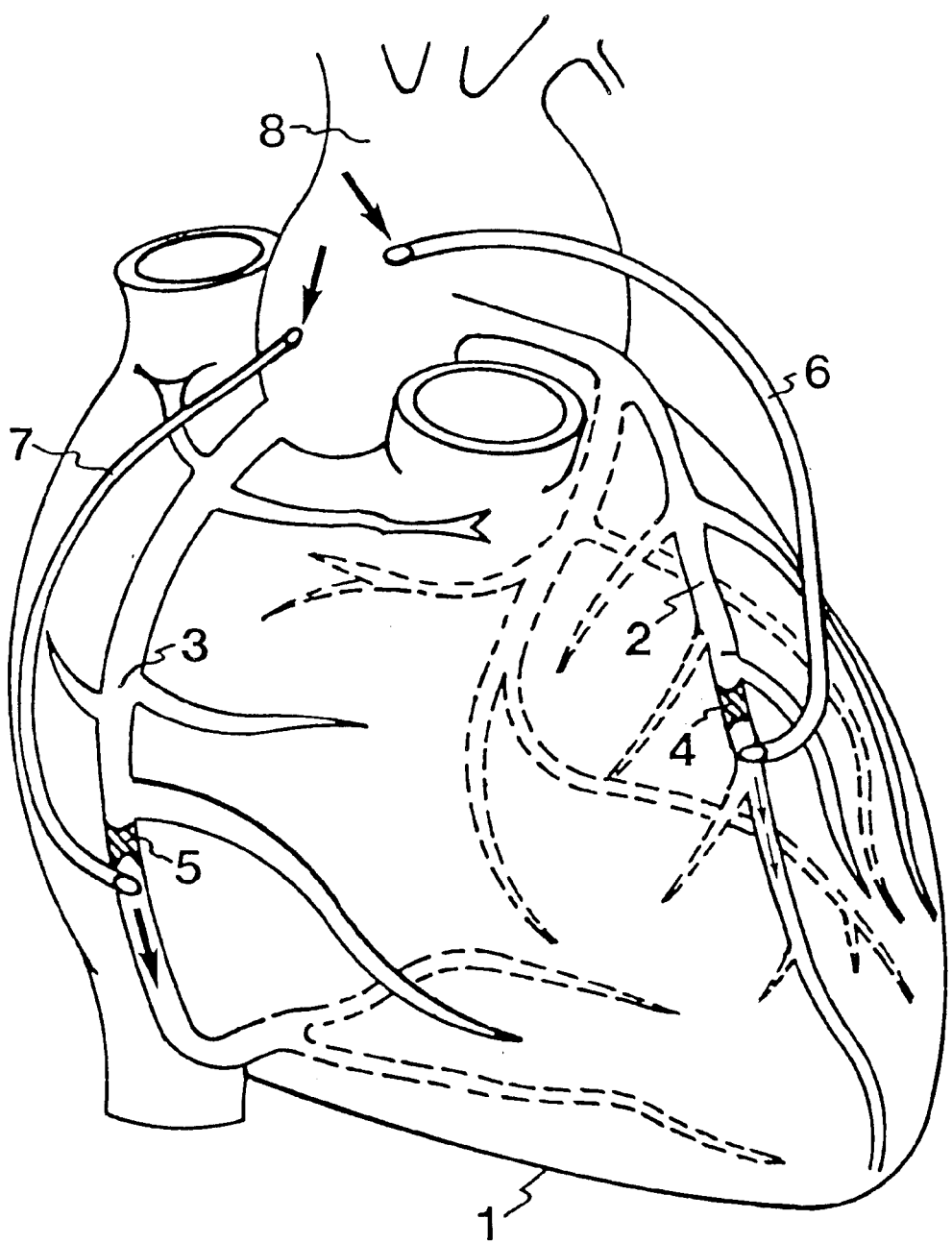
FIG. 1 is a perspective view and shows a heart with two schematically indicated bypasses of coronary vessels each having a blocking.

The heart 1 shown in FIG. 1 has two coronary vessels 2, 3 each having a blocking 4, 5, i.e. a stenosis or an occlusion. FIG. 1 illustrates schematically how these blockings are bypassed by means of two vessels 6, 7 which can be taken from the patient himself. More specifically, one end of the vessel 6 is connected after the blocking 4, seen in the normal direction of flow in the vessel 2, and its other end is connected to the aorta 8, such that a sufficient quantity of oxygen-rich blood will be supplied to the already blocked coronary vessel 2 after the blocking 4 therein. The same applies to the vessel 3.

For effecting the connection of the vessel 6 to the coronary vessel 2, the embodiment shown in FIGS. 2–5 of a branching device according to the invention can be used. The main components of this branching device are a sleeve 10 and a collar 11 fixed thereto. The sleeve 10 preferably consists of metal, e.g. titanium, or some other material that is not rejected by the body tissue. Its construction is such as to be expandable or radially extensible, i.e. its diameter can be increased. Moreover, the sleeve 10 is permanently deformable and thus retains its shape after such an expansion.

A suitable material for the sleeve 10 is a net or some other material that permits said permanent deformation, i.e. an increase of the diameter of the sleeve 10, said increase normally being accompanied by a corresponding decrease of the length of the sleeve 10. A particularly suitable material is the so-called stent material, which is used in sleeves for expansion of constricted blood vessels.

According to the invention, the sleeve 10 further has an axially elongate opening 12, whose dimensions, when expanding the sleeve 10, will be distorted in a manner similar to the distortion of the actual sleeve 10, i.e. a shortening in the axial direction and an expansion in the circumferential direction. The opening 12 will thus obtain a decreased length in the axial direction of the sleeve 10, but an increased width in the circumferential direction of the sleeve 10.

The collar 11 consists of a fluid-tight and preferably flexible or even elastic material, which of course must also be such as not to risk being rejected by the body tissue. More specifically, the collar 11 has a shoulder portion 13 and a neck portion 14.

The shoulder portion 13 has a shape substantially conforming to the shape of the sleeve 10. It has such a size as to overlap the opening 12 and thus extend over the sleeve 10 around the opening 12. The overlapping is also so great as to remain also in case of a certain change of the size of the opening 12, as will be described below. The shoulder portion 13 can also completely encompass at least part of or the entire sleeve 10, in which case the material of the shoulder portion 13 is so elastic as not to essentially counteract an expansion of the sleeve 10, as will be described below.

The neck portion 14 of the collar 11 is a direct extension of the shoulder portion 13 and essentially has the shape of a cylinder. The most important function of the neck portion 14 is to serve as connecting member for the new vessel 6.

Figure 2:
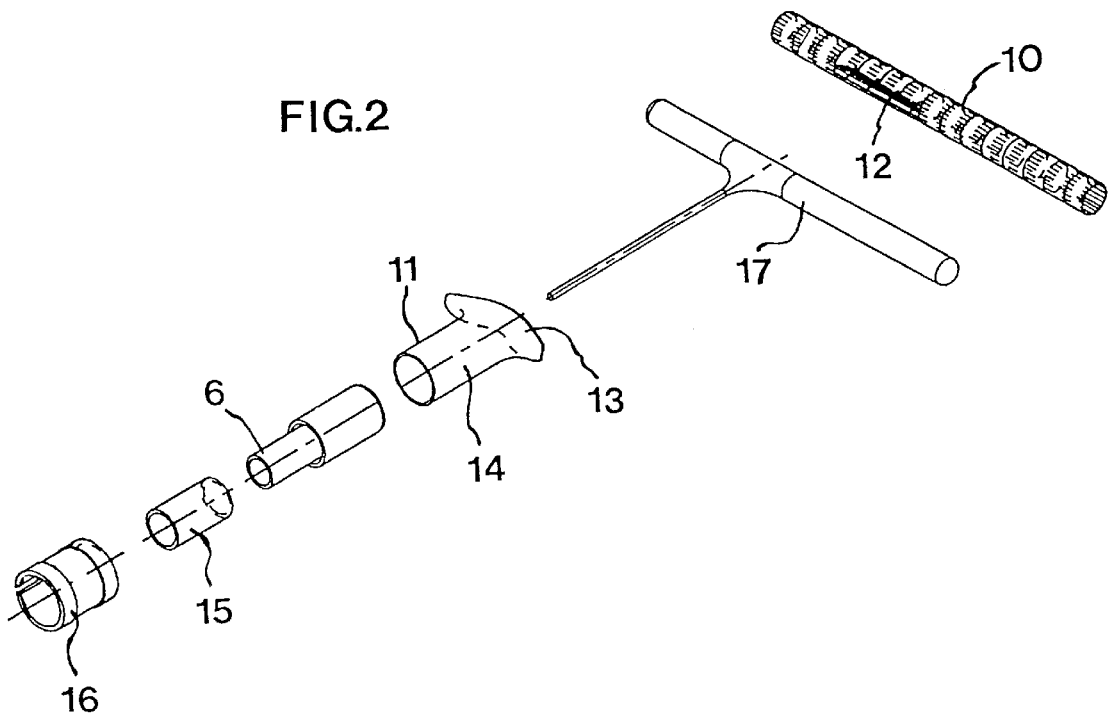
FIG. 2 is a perspective view and shows, among other things, a few parts included in one embodiment of a branching device according to the invention.

For the connection between the neck portion 14 and the vessel 6, a rigid supporting sleeve 15 and a clamping or locking sleeve 16 can be used according to the embodiment illustrated in the drawings. The end of the vessel 6 is adapted to be inserted into and through the supporting sleeve 15, and the outermost part of the vessel 6 is then to be folded or pulled back over the outside of the supporting sleeve 15. This folding back of the end of the vessel 6 is shown in FIG. 2, but with the supporting sleeve 15 separated from the vessel 6. For completion of the connection, the supporting sleeve 15 with the pulled-on vessel 6 is inserted into the open end of the neck portion 14. Then the clamping sleeve 16 is arranged and clamped around the neck portion 14, which then together with the interiorly situated, folded-back part of the vessel 6 is pressed against the outside of the supporting sleeve 15. As a result, a fixed and tight connection between the neck portion 14 and the vessel 6 is achieved.

The actual clamping sleeve 16 is advantageously divisible so as to be laterally movable over the neck portion 14 before the clamping operation, which suitably is effected by the clamping sleeve 16 having, at its ends that are free before clamping, hooks engaging each other and permitting an easy tightening of the clamping sleeve 16 around the neck portion 14.

For fixing the sleeve 10 and the collar 11 relative to e.g. the blood vessel 2 in FIG. 1, use is made of a T-shaped balloon 17, the opening of which is situated on that branch of the balloon which extends through the neck portion 14. By means of this balloon 17, the sleeve 10 can be expanded in its place within the blood vessel 2, such that the blood vessel expands and thus is pressed against the sleeve 10 for fixing the position thereof in the blood vessel 2. At the same time the collar 11 will be squeezed between the blood vessel 2 and the sleeve 10, such that the position of the collar 11 will be safely fixed relative to the blood vessel 2 and a fluid-tight seal between this and the collar 11 is obtained without necessitating any suture.

The balloon 17 can, as shown, be a single balloon, but alternatively it can be formed of two elongated balloons extending through the neck portion 14 and in different directions from the neck portion 14 through the sleeve 10, so as to be inflatable via the neck portion 14 and, during inflation, expand the sleeve 10 in essentially the same fashion as in the case where the balloon 17 is a single balloon.

Figure 3:
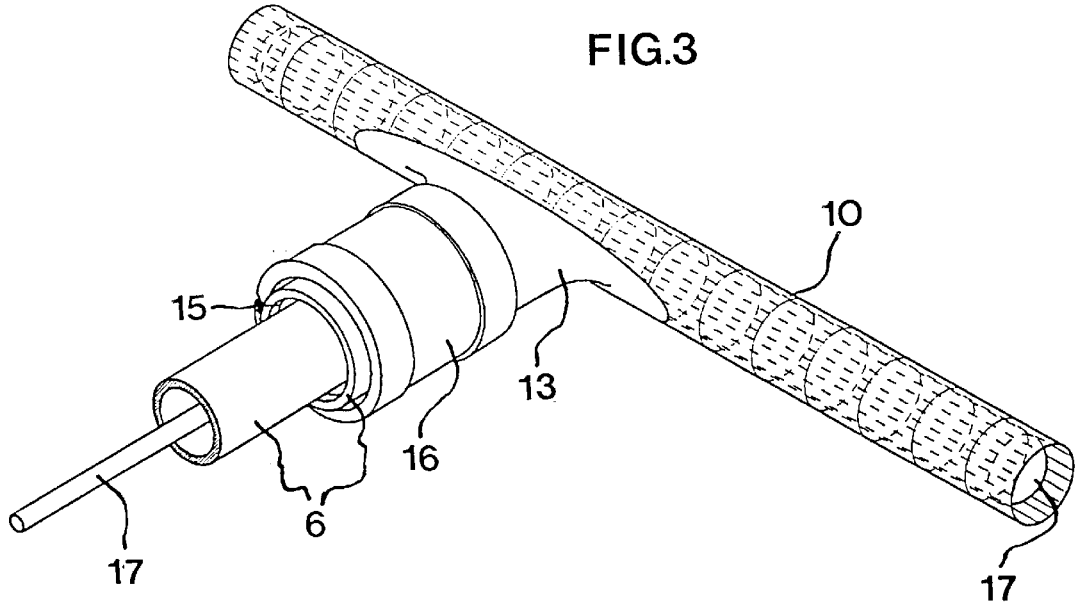
FIG. 3 shows some of the parts in FIG. 2 in an assembled state before insertion into a blocked vessel.

It is possible to first prepare the connection between the collar 11 and the new vessel 6 with the balloon 17 situated inside the sleeve 10 and extending through the blood vessel 6 and out of the opposite end thereof, as shown in FIG. 3. Subsequently, the sleeve 10 can in a reciprocating movement be inserted into, for instance the vessel 2 through an opening 18 formed therein through a longitudinal incision, as shown in FIG. 4. Then the branching device is fixed in the vessel 2 by inflating the balloon 17, whereby the sleeve 10 is expanded and shortened as shown in FIG. 5. Finally, the balloon 17 can be deflated and then be pulled out through the collar 11 and the vessel 6.

For completion of the operation, the free end of the new vessel 6 is to be connected to a blood vessel, for instance the aorta 8, which can give a sufficient flows of blood to the vessel 2 after the blocking 4.

An alternative method of carrying out a bypass operation by means of the branching device according to the invention comprises the following steps.

Also in this case, the sleeve 10 is inserted in the vessel 2 through the opening 18 thereof, however without first connecting the vessel 6 with the collar 11. The fixing of the sleeve 10 in relation to the blood vessel 2 is carried out by inflation of the balloon 17 also in this case, and then the balloon is removed by being opened and pulled out through the collar 11. Finally the new vessel 6, which has previously been connected to a blood vessel, for instance the aorta 8, which can give a sufficient flow of blood to the vessel 2 after the blocking 4, and the neck portion 14 are connected by means of the supporting sleeve 15 and the clamping sleeve 16 in the same manner as described above.

It should be emphasised that in the two methods as described above, the collar 11 is even from the beginning fixed to the sleeve 10, and the ballon 17 is also even from the beginning inserted in the sleeve 10.

The expert realises that several modifications of the above-described embodiment of a branching device are conceivable within the scope of the invention as defined in the appended claims.

What is claimed is:

1. A system including a branching device for a blood vessel, comprising a sleeve, which is radially extensible and has an opening in its circumferential surface, characterised by a collar which consists of a fluid-tight material and is fixed to the sleeve before the branching device is used and which has a shoulder portion extending at least around the opening in the circumferential surface of the sleeve, and, a neck portion integral with the shoulder portion and projecting radially from the opening in the circumferential surface of the sleeve; and a balloon inserted in the sleeve and inflatable through the neck portion.

2. A system as claimed in claim 1, characterised in that the opening in the circumferential portion of the sleeve is unsymmetrically positioned relative to ends of the sleeve.

3. A system as claimed in claim 1, characterized in that the sleeve consists of a net material.

4. A system as claimed in claim 3, characterised in that the sleeve consists of a material suitable for stents.

5. A system as claimed in claim 1, characterized in that the shape of the sleeve is essentially deformable in shape when increasing the diameter of the sleeve and, after deformation, maintaining an after-deformation shape.

6. A system as claimed in claim 1, characterized in that the collar consists of an elastic material.

7. A system as claimed in claim 1, characterised in that the shoulder portion of the collar is attached to the outside of the sleeve.

8. A system as claimed in claim 1, characterised in that the balloon is T-shaped.

9. A system as claimed in claim 1, characterized in that the shoulder portion fully circumferentially surrounds at least an axially extending part of the sleeve.

10. A system as claimed in claim 2, characterized in that the sleeve consists of a net material.

11. A system as claimed in claim 10, characterized in that the collar consists of an elastic material.

12. A system as claimed in claim 11, characterized in that the shoulder portion of the collar 11 is attached to the outside of the sleeve 10.

13. A system as claimed in claim 12, characterized in that the balloon is T-shaped.

14. A system as claimed in claim 13, characterized in that the shoulder portion fully circumferentially surrounds at least an axially extending part of the sleeve.

15. A system as claimed in claim 2, characterized in that the shoulder portion of the collar is attached to the outside of the sleeve.

16. A system as claimed in claim 2, characterized in that the balloon is T-shaped.

17. A system as claimed in claim 2, characterized in that the shoulder portion fully circumferentially surrounds at least an axially extending part of the sleeve.

* * * * *